(12) United States Patent
Kottari et al.

(10) Patent No.: US 11,541,382 B2
(45) Date of Patent: Jan. 3, 2023

(54) PROCESS FOR THE PREPARATION OF HYDROCARBON SOLUBLE ORGANOMETALLIC CATALYSTS

(71) Applicant: Hindustan Petroleum Corporation Limited, Bangalore (IN)

(72) Inventors: Naresh Kottari, Bangalore (IN); Kanuparthy Naga Raja, Bangalore (IN); Siva Kesava Raju Chintalapati, Bangalore (IN); Satyanarayana Murty Pudi, Bangalore (IN); Bhavesh Sharma, Bangalore (IN); Ramkumar Mangala, Bangalore (IN); Peddy Venkata Chalapathi Rao, Bangalore (IN); Nettam Venkateswarlu Choudary, Bangalore (IN); Sriganesh Gandham, Bangalore (IN)

(73) Assignee: Hindustan Petroleum Corporation Limited, Bangalore (IN)

( * ) Notice: Subject to any disclaimer, the term of this patent is extended or adjusted under 35 U.S.C. 154(b) by 356 days.

(21) Appl. No.: 16/622,683

(22) PCT Filed: Nov. 7, 2017

(86) PCT No.: PCT/IN2017/050512
§ 371 (c)(1),
(2) Date: Dec. 13, 2019

(87) PCT Pub. No.: WO2018/235094
PCT Pub. Date: Dec. 27, 2018

(65) Prior Publication Data
US 2021/0138442 A1    May 13, 2021

(30) Foreign Application Priority Data
Jun. 19, 2017 (IN) .............................. 201741021461

(51) Int. Cl.
| | | |
|---|---|---|
| B01J 31/22 | (2006.01) | |
| B01J 37/04 | (2006.01) | |
| C07F 15/02 | (2006.01) | |
| C07F 15/04 | (2006.01) | |
| C07F 15/06 | (2006.01) | |
| C10G 47/02 | (2006.01) | |

(52) U.S. Cl.
CPC ......... B01J 31/223 (2013.01); B01J 31/2226 (2013.01); B01J 37/04 (2013.01); C07F 15/02 (2013.01); C07F 15/04 (2013.01); C07F 15/06 (2013.01); C10G 47/02 (2013.01); *B01J 2231/641* (2013.01); *B01J 2531/842* (2013.01); *B01J 2531/845* (2013.01); *B01J 2531/847* (2013.01)

(58) Field of Classification Search
CPC ........ C07F 15/02; C07F 15/025; C07F 15/04; C07F 15/045; C07F 15/06; C07F 15/065; C10G 47/02
See application file for complete search history.

(56) References Cited

U.S. PATENT DOCUMENTS

| | | | | | |
|---|---|---|---|---|---|
| 3,935,228 | A | * | 1/1976 | Keblys | C07F 15/065 554/131 |
| 4,225,743 | A | * | 9/1980 | Hoshiyama | C07C 2/30 585/512 |
| 7,524,338 | B2 | * | 4/2009 | Pedrazzini | C10L 1/143 44/365 |
| 8,097,149 | B2 | | 1/2012 | Wu et al. | |
| 8,445,399 | B2 | | 5/2013 | Wu et al. | |
| 9,403,153 | B2 | | 8/2016 | Qiu et al. | |
| 10,829,504 | B2 | * | 11/2020 | Sakuta | C07F 7/0838 |
| 10,906,857 | B2 | * | 2/2021 | Back | C07C 49/76 |
| 2009/0308792 | A1 | * | 12/2009 | Wu | B01J 31/04 208/243 |
| 2012/0152806 | A1 | | 6/2012 | Reynolds et al. | |
| 2013/0150605 | A1 | * | 6/2013 | Sydora | C07F 13/005 556/61 |
| 2019/0330543 | A1 | * | 10/2019 | Raja | C10G 45/10 |
| 2020/0216378 | A1 | * | 7/2020 | Back | C07C 51/38 |
| 2021/0146345 | A1 | * | 5/2021 | Kottari | B01J 37/04 |

FOREIGN PATENT DOCUMENTS

| | | | |
|---|---|---|---|
| JP | 53137857 A | * | 12/1978 |
| JP | H02288842 A | | 11/1990 |
| JP | 07252186 A | * | 10/1995 |
| JP | 2015-527452 A | | 9/2015 |

OTHER PUBLICATIONS

M. Amoruso et al., 27 International Journal of Toxicology, 97-165 (2008) (Year: 2008).*
A. Phenix, "Generic Hydrocarbon Solvents: a Guide to Nomenclature", 29 WAAC News Letter, 13-22 (2007) (Year: 2007).*
English-language translation of K. Yamaguchi JP 53137857 (1979) by LinguaLinx Language Solutions, Inc. (Jan. 2022) (Year: 2022).*
M. Elizalde et al., 4 Polyhedron, 3097-2101 (1985) (Year: 1985).*
T. Sugimura et al., 11 Journal of Dispersion Science and Technology, 195-214 (1990) (Year: 1990).*
T. Sugimura. Nippon Kagaku Kaishi , 1249-1253 (1983) (Year: 1983).*

(Continued)

*Primary Examiner* — Alexander R Pagano
(74) *Attorney, Agent, or Firm* — Marshall, Gerstein & Borun LLP

(57) ABSTRACT

The instant disclosure provides a process for synthesis of compound of Formula:

$$X_a\text{-}M^{z+}\text{-}Y_b,$$

wherein $M^{z+}$ is a transition metal ion and X and Y are carboxylate anions. The catalysts are hydrocarbon soluble and the process for their preparation, as disclosed herein, constitutes an elegant method for the preparation of such catalysts.

6 Claims, No Drawings

(56) References Cited

OTHER PUBLICATIONS

E. Glebov et al., 10 Photochem. Photobiol. Sci., 425-430 (2011) (Year: 2011).*
L. Huang et al., European Journal of Inorganic Chemistry, 5718-5727 (2013) (Year: 2013).*
International Search Report and Written Opinion for Application No. PCT/IN2017/050512, dated Jan. 24, 2018.

* cited by examiner

PROCESS FOR THE PREPARATION OF HYDROCARBON SOLUBLE ORGANOMETALLIC CATALYSTS

FIELD OF THE INVENTION

The present disclosure in general relates to the field of organometallic catalysts, and in particular to a process for the preparation of organometallic catalysts. The disclosure provides a mild, energy-frugal and hence cost-effective process for the preparation of organometallic catalysts.

BACKGROUND OF THE INVENTION

Refined fossil fuels are one of the most precious resources available to humankind to satisfy its energy requirements. However, given the global rise in population, the demand for refined fossil fuels is fast outpacing supply, which has led researchers to look for a solution for this possible fuel crunch which might knock at the door sometime soon in the near future. One approach to this problem has been converting heavy oil, which is as such unsuitable for use in place of refined fuels, into lighter, low boiling fractions which can be valuable as fuels. Heavy oils are those that boil at or above 524° C. The process most frequently resorted to, for converting heavy oils to lighter fractions, is catalytic hydrocracking, wherein a catalyst (mostly an organometallic one) transforms the high boiling heavy oil fractions into lighter ones.

Many organometallic catalysts have been used for this purpose, and most of them comprise a transition metal and an organic ligand. Catalysts containing more than one transition metal and multiple organic ligands are also known.

For instance, U.S. Pat. No. 9,403,153B2 discloses a molybdenum containing catalyst for heavy oil cracking, and a process for the preparation of the catalyst.

Another U.S. Pat. No. 8,445,399B2 describes a similar hydrocarbon soluble molybdenum catalyst and a process for the preparation of the same.

U.S. Pat. No. 8,097,149B2 discloses a bimetallic/multimetallic catalyst for hydrodesulfurization of petroleum feedstock. The application also describes a method for the preparation of said catalyst.

However, most of these catalysts are difficult to prepare, in that the temperatures at which they are synthesized are generally about 100° C. or higher. This might not seem like a major concern if one envisages a lab scale synthesis, but a lab scale synthesis seldom helps in such cases, given the enormity of scale at which hydrocracking needs to be done, in order to keep the process economically viable and in order to cater to the humongous fuel requirements. Such high scale operations call for higher quantities of catalysts. Making these catalysts on higher scale at the high temperatures as mentioned above, is an energy-sapping process, which eventually leads to cost overruns.

In view of all the aforementioned facts, a mild and ambient, low temperature process for the synthesis of hydrocarbon soluble organometallic catalysts suitable for hydrocracking of heavy oil, will be a valuable addition to the arsenal of existing methods.

SUMMARY OF THE INVENTION

In an aspect of present disclosure, there is provided a process for synthesis of compound of Formula:

$X_a\text{-}M^{z+}\text{-}Y_b$, wherein $M^{z+}$ is a transition metal ion, wherein z is in the range of 1-9; X and Y are anions of Formula $R1(COO-)_c$ and $R2(COO-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)c and salts of R2(COOH)d; (iii) water; and (iv) at least one organic solvent to obtain a first mixture; and (b) stirring the first mixture to obtain the compound.

In an aspect of present invention, there is provided a compound of Formula:

$X_a\text{-}M^{z+}\text{-}Y_b$, wherein $M^{z+}$ is $Fe^{3+}$; X and Y are independently selected from the group consisting of 2-ethyl hexyl carboxylate and tridecanoate; and 'a' and 'b' are in the range of 0-3, and have values such that $X_a\text{-}M^{z+}\text{-}Y_b$ is a neutral molecule.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or steps.

The term "including" is used to mean "including but not limited to", "including" and "including but not limited to" are used interchangeably.

The term "alkyl" refers to straight or branched aliphatic hydrocarbon chain having the 1-16 carbon atoms. This term is exemplified by groups such as n-butyl, iso-butyl, t-butyl, n-hexyl and the like. The groups may be optionally substituted.

The term "aryl" refers to aromatic radicals having 5 to 22 carbon atoms having a single ring (e.g. phenyl) or multiple rings (e.g. biphenyl), or multiple condensed (fused) rings (e.g. naphthyl or anthranyl), which may be optionally substituted by one or more substituents. Preferred aryl groups, without limitation, include phenyl, naphthyl, indanyl, biphenyl and the like.

"Halo" or "Halogen", alone or in combination with any other term means halogens such as chloro (Cl), fluoro (F), bromo (Br) and iodo (I).

The term "haloalkyl" embraces radicals wherein any one or more of the $C_{1-16}$ alkyl carbon atoms is substituted with halo as defined above.

The term "cycloalkyl" refers to non-aromatic mono or polycyclic ring system of about 3 to 12 carbon atoms, which may be optionally substituted by one or more substituents. The polycyclic ring denotes hydrocarbon systems containing two or more ring systems with one or more ring carbon atoms in common, i.e., a spiro, fused or bridged structures. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g. spiro [4.4] non-2-yl and the like.

The term "heteroaryl" refers to a heteroaromatic carbocyclic group of 1 to 20 carbon atoms having a single ring (e.g. pyridine) or multiple rings (e.g. isoquinoline), or multiple condensed (fused) rings. Preferred heteroaryls include thiophene, pyrazole, thiazole, pyridine and the like. The groups may be optionally substituted.

Furthermore, the term "heterocyclyl" refers to a stable 2 to 6 membered rings radical, which consists of 1-20 carbon atoms and from one to five heteroatoms selected from nitrogen, phosphorus, oxygen and sulfur. For purposes of this invention the heterocyclic ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. Preferred heterocyclyl groups, without limitation, include azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyrazolyl, pyridyl, pteridinyl, purinyl, quinazolinyl, qunioxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl and isochromanyl. The groups may be optionally substituted.

The term "alkanediyl" refers to a divalent saturated aliphatic group having 1-16 carbon atoms, with one or two saturated carbon atom(s) as the point(s) of attachment, The groups, —CH$_2$— (methylene), —CH$_2$CH$_2$—, —CH$_2$C(CH$_3$)$_2$CH$_2$—, —CH$_2$CH$_2$CH$_2$— are non-limiting examples of alkanediyl groups. The groups may be optionally substituted.

The term "arylene" refers to an aromatic group where two hydrogen atoms are removed allowing for a group to be substituted at the position where the two hydrogen atoms were removed, and having 5 to 22 carbon atoms. The groups may be optionally substituted.

The term "haloalkanediyl" refers to a divalent saturated aliphatic group having 1-16 carbon atoms, with one or two saturated carbon atom(s) as the point(s) of attachment, and wherein any one or more of the $C_{1-16}$ alkyl carbon atoms is substituted with 'halo' as defined above. The groups may be optionally substituted.

The term "cycloalkanediyl" refers to a diradical saturated monocyclic or polycyclic hydrocarbon group. Examples of "cycloalkanediyl" include, without limitation, 'cyclopropanediyl', and 'cyclobutanediyl'. The groups may be optionally substituted.

The term "heteroarenediyl" refers to a divalent heteroaromatic carbocyclic group of 1 to 20 carbon atoms having a single ring (e.g. pyridine) or multiple rings (e.g. isoquinoline), or multiple condensed (fused) rings. The groups may be optionally substituted.

The term "heterocyclicdiyl" refers to a divalent, stable 2 to 6 membered rings radical, which consists of 1-20 carbon atoms and from one to five heteroatoms selected from nitrogen, phosphorus, oxygen and sulfur. For purposes of this invention the heterocyclicdiyl ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. The groups may be optionally substituted.

Unless defined otherwise, all technical and scientific terms used herein have the same meaning as commonly understood to one of ordinary skill in the art to which this disclosure belongs. Although methods and materials similar or equivalent to those described herein can be used in the practice or testing of the disclosure, the preferred methods, and materials are now described. All publications mentioned herein are incorporated herein by reference.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 70 wt % to about 95 wt % should be interpreted to include not only the explicitly recited limits of about 70 wt % to about 95 wt %, but also to include sub-ranges, such as 70.05 wt % to 91 wt %, 70 wt % to 85 wt %, and so forth, as well as individual amounts, including fractional amounts, within the specified ranges, such as 70.5 wt %, 81.1 wt %, and 92.9 wt %, for example.

The present disclosure is not to be limited in scope by the specific embodiments described herein, which are intended for the purposes of exemplification only. Functionally equivalent products, compositions, and methods are clearly within scope of the disclosure, as described herein.

As already discussed above, heavy oil upgrade is valuable process for transforming high boiling and less useful heavy oils into lower boiling and valuable products. Catalysts (mostly transition metal organometallic) used for this purpose are almost invariably synthesized at higher temperature, thereby leading to high energy consumption. Thus, a process for the synthesis of organometallic catalysts for heavy oil upgrade, which uses lower temperatures is very much required. The present disclosure provides a process for the synthesis of transition metal catalysts, at lower temperatures.

In an embodiment of present disclosure, there is provided a process for synthesis of compound of Formula:

$$X_a\text{-}M^{z+}\text{-}Y_b,$$

wherein $M^{z+}$ is a transition metal ion, wherein z is in the range of 1-9; X and Y are anions of Formula $R1(COO^-)_c$ and $R2(COO^-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)c and salts of R2(COOH)d; (iii) water; and (iv) at least one organic solvent to obtain a first mixture; and (b) stirring the first mixture to obtain the compound.

In another embodiment of present disclosure, there is provided a process as described herein, wherein the: (a) transition metal salt to at least one carboxylate salt molar ratio in the first mixture is in the range of 1:2-1:6; (b) transition metal salt to water moles to volume ratio in the first mixture is in the range of 1:1.5-1:2; and (c) transition metal salt to at least one organic solvent moles to volume ratio in the first mixture is in the range of 1:2-1:4.

In yet another embodiment of present disclosure, there is provided a process as described herein, wherein the salts of $R1(COOH)_c$ and the salts of $R2(COOH)_d$ are independently selected from the group consisting of lithium salt, sodium salt, potassium salt, trialkylammonium salts, quaternary alkylammonium salts, and combinations thereof.

In an embodiment of present disclosure, there is provided a process as described herein, wherein the at least one organic solvent is selected from the group consisting of hexane, toluene, xylenes, diesel, kerosene, naphtha, and combinations thereof.

In another embodiment of present disclosure, there is provided a process as described herein, wherein: contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$; (iii) water; and (iv) at least one organic solvent to obtain a first mixture is carried out at a temperature in the range of 30-80° C.

In yet another embodiment of present disclosure, there is provided a process as described herein, wherein: contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$; (iii) water; and (iv) at least one organic solvent to obtain a first mixture is carried out at a temperature of 40° C.

In an embodiment of present disclosure, there is provided a process as described herein, wherein stirring the first mixture to obtain the compound is carried out at a temperature in the range of 30-80° C. for a period in the range of 1-10 hours.

In another embodiment of present disclosure, there is provided a process as described herein, wherein stirring the first mixture to obtain the compound is carried out at a temperature of 40° C. for a period of 3 hours.

In yet another embodiment of present disclosure, there is provided a compound of Formula:

$$X_a\text{-}M^{z+}\text{-}Y_b,$$

wherein $M^{z+}$ is $Fe^{3+}$; X and Y are independently selected from the group consisting of 2-ethyl hexyl carboxylate and tridecanoate; and 'a' and 'b' are in the range of 0-3, and have values such that $X_a\text{-}M^{z+}\text{-}Y_b$ is a neutral molecule.

In an embodiment of present disclosure, there is provided a process for synthesis of compound of Formula:

$$X_a\text{-}M^{z+}\text{-}Y_b,$$

wherein $M^{z+}$ is a transition metal ion, wherein 'z' is in the range of 1-9; X and Y are anions of Formula $R1(COO^-)_c$ and $R2(COO^-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of C1-16 alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that Xa-$M^{z+}$-Yb is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture to obtain the compound, wherein the: (a) transition metal salt to at least one carboxylate salt molar ratio in the first mixture is in the range of 1:2-1:6; (b) transition metal salt to water moles to volume ratio in the first mixture is in the range of 1:1.5-1:2; and (c) transition metal salt to at least one organic solvent moles to volume ratio in the first mixture is in the range of 1:2-1:4.

In an embodiment of present disclosure, there is provided a process for synthesis of compound of Formula:

$$X_a\text{-}M^{z+}\text{-}Y_b,$$

wherein $M^{z+}$ is a transition metal ion, wherein 'z' is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that Xa-Mz+-Yb is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture to obtain the compound, wherein the: (a) transition metal salt to at least one carboxylate salt molar ratio in the first mixture is in the range of 1:2-1:5.5; (b) transition metal salt to water moles to volume ratio in the first mixture is in the range of 1:1.5-1:2; and (c) transition metal salt to at least one organic solvent moles to volume ratio in the first mixture is in the range of 1:2-1:4.

In an embodiment of present disclosure, there is provided a process for synthesis of compound of Formula:

$$X_a\text{-}M^{z+}\text{-}Y_b,$$

wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture to obtain the compound, wherein the: (a) transition metal salt to at least one carboxylate salt molar ratio in the first mixture is in the range of 1:2-1:6; (b) transition metal salt to water moles to volume ratio in the first mixture is in the range of 1:1.5-1:1.9; and (c) transition metal salt to at least one organic solvent moles to volume ratio in the first mixture is in the range of 1:2-1:4.

In an embodiment of present disclosure, there is provided a process for synthesis of compound of Formula:

$$X_a\text{-}M^{z+}\text{-}Y_b,$$

wherein Mz+ is a transition metal ion, wherein z is in the range of 1-9; X and Y are anions of Formula R1(COO—)$_c$ and R2(COO—)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture to obtain the compound, wherein the: (a) transition metal salt to at least one carboxylate salt molar ratio in the first mixture is in the range of 1:2-1:6; (b) transition metal salt to water moles to volume ratio in the first mixture is in the range of 1:1.5-1:2; and (c) transition metal salt to at least one organic solvent moles to volume ratio in the first mixture is in the range of 1:2-1:3.9.

In an embodiment of present disclosure, there is provided a process for synthesis of compound of Formula:

$$X_a\text{-}M^{z+}\text{-}Y_b,$$

wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a$-$M^{z+}$-$Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture to obtain the compound, wherein the salts of R1(COOH)$_c$ and the salts of R2(COOH)$_d$ are independently selected from the group consisting of lithium salt, sodium salt, potassium salt, trialkylammonium salts, quaternary alkylammonium salts, and combinations thereof.

In an embodiment of present disclosure, there is provided a process for synthesis of compound of Formula:

$X_a$-$M^{z+}$-$Y_b$, wherein $M^{z+}$ is a transition metal ion, wherein 'z' is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a$-$M^{z+}$-$Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent selected from the group consisting of hexane, toluene, xylenes, petroleum fractions like diesel, kerosene, naphtha, and combinations thereof, to obtain a first mixture; and (b) stirring the first mixture to obtain the compound.

In an embodiment of present disclosure, there is provided a process for synthesis of compound of Formula:

$X_a$-$M^{z+}$-$Y_b$, wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a$-$M^{z+}$-$Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent at a temperature in the range of 30-80° C., to obtain a first mixture; and (b) stirring the first mixture to obtain the compound.

In an embodiment of present disclosure, there is provided a process for synthesis of compound of Formula:

$X_a$-$M^{z+}$-$Y_b$, wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a$-$M^{z+}$-$Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent at a temperature in the range of 30-70° C., to obtain a first mixture; and (b) stirring the first mixture to obtain the compound.

In an embodiment of present disclosure, there is provided a process for synthesis of compound of Formula:

$X_a$-$M^{z+}$-$Y_b$, wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a$-$M^{z+}$-$Y_b$ is a neutral molecule;

the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent at a temperature in the range of 30-60° C., to obtain a first mixture; and (b) stirring the first mixture to obtain the compound.

In an embodiment of present disclosure, there is provided a process for synthesis of compound of Formula:

wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that X$_a$-M$^{z+}$-Y$_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent at a temperature in the range of 30-50° C., to obtain a first mixture; and (b) stirring the first mixture to obtain the compound.

In an embodiment of present disclosure, there is provided a process for synthesis of compound of Formula:

wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that X$_a$-M$^{z+}$-Y$_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent, at a temperature of 40° C. to obtain a first mixture; and (b) stirring the first mixture to obtain the compound.

In an embodiment of present disclosure, there is provided a process for synthesis of compound of Formula:

wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that X$_a$-M$^{z+}$-Y$_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture at a temperature in the range of 30-80° C. for a period in the range of 1-10 hours to obtain the compound.

In an embodiment of present disclosure, there is provided a process for synthesis of compound of Formula:

wherein $M^{z+}$ is a transition metal ion, wherein z is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that X$_a$-M$^{z+}$-Y$_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$; (iii) water; and (iv) at least one organic solvent to obtain a first mixture; and (b) stirring the first mixture at a temperature in the range of 30-70° C. for a period in the range of 1-9 hours to obtain the compound.

In an embodiment of present disclosure, there is provided a process for synthesis of compound of Formula:

wherein $M^{z+}$ is a transition metal ion, wherein z is in the range of 1-9; X and Y are anions of Formula $R1(COO^-)_c$ and $R2(COO^-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$; (iii) water; and (iv) at least one organic solvent to obtain a first mixture; and (b) stirring the first mixture at a temperature in the range of 30-60° C. for a period in the range of 1-7 hours to obtain the compound.

In an embodiment of present disclosure, there is provided a process for synthesis of compound of Formula:

wherein $M^+$ is a transition metal ion, wherein z is in the range of 1-9; X and Y are anions of Formula $R1(COO^-)_c$ and $R2(COO^-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$; (iii) water; and (iv) at least one organic solvent to obtain a first mixture; and (b) stirring the first mixture at a temperature in the range of 30-50° C. for a period in the range of 1-6 hours to obtain the compound.

In an embodiment of present disclosure, there is provided a process for synthesis of compound of Formula:

wherein $M^{z+}$ is a transition metal ion, wherein z is in the range of 1-9; X and Y are anions of Formula $R1(COO^-)_c$ and $R2(COO^-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$; (iii) water; and (iv) at least one organic solvent to obtain a first mixture; and (b) stirring the first mixture at a temperature in the range of 30-45° C. for a period in the range of 1-4 hours to obtain the compound.

In an embodiment of present disclosure, there is provided a process for synthesis of compound of Formula:

wherein $M^{z+}$ is a transition metal ion, wherein z is in the range of 1-9; X and Y are anions of Formula $R1(COO^-)_c$ and $R2(COO^-)_d$ respectively, wherein 'c' and 'd' are independently in the range of 1-2; when 'c' is 1, R1 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'c' is 2, R1 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; when 'd' is 1, R2 is selected from the group consisting of $C_{1-16}$ alkyl, $C_{5-22}$ aryl, $C_{1-16}$ haloalkyl, $C_{3-12}$ cycloalkyl, $C_{1-20}$ heteroaryl, and $C_{1-20}$ heterocyclyl; when 'd' is 2, R2 is selected from the group consisting of $C_{1-16}$ alkanediyl, $C_{5-22}$ arylene, $C_{1-16}$ haloalkanediyl, $C_{3-12}$ cycloalkanediyl, $C_{1-20}$ heteroarenediyl, $C_{1-20}$ heterocyclicdiyl; 'a' and 'b' are in the range of 0-9, wherein 'a' and 'b' have values such that $X_a\text{-}M^{z+}\text{-}Y_b$ is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$; (iii) water; and (iv) at least one organic solvent to obtain a first mixture; and (b) stirring the first mixture at a temperature of 40° C. for a period of 3 hours to obtain the compound.

In an embodiment of present disclosure, there is provided a compound of Formula:

wherein $M^{z+}$ is $Fe^{3+}$; X and Y are independently selected from the group consisting of 2-ethyl hexyl carboxylate and tridecanoate; and 'a' and 'b' are in the range of 0 3, and have values such that $X_a\text{-}M^{z+}\text{-}Y_b$ is a neutral molecule; prepared using a process comprising the steps of: (a) contacting (i) a transition metal salt of Formula M-S, wherein M is 'Fe' and S is a ligand selected from the group consisting of nitrate, sulfate, chloride, sulfite, and nitrite; (ii) a combination of salts of R1(COOH)$_c$ and R2(COOH)$_d$, wherein R1(COOH)$_c$ and R2(COOH)$_d$ are 2-ethylhexanoic acid and tridecanoic acid respectively; (iii) water; and (iv) at least one organic solvent to obtain a first mixture; and (b) stirring the first mixture to obtain the compound.

In an embodiment of present disclosure, there is provided a process for synthesis of compound of Formula:

$$X_a\text{-}M^{z+}\text{-}Y_b,$$

wherein $M^{z+}$ is a transition metal ion, wherein 'z' is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of C$_{1-16}$ alkyl, C$_{5-22}$ aryl, C$_{1-16}$ haloalkyl, C$_{3-12}$ cycloalkyl, C$_{1-20}$ heteroaryl, and C$_{1-20}$ heterocyclyl; when 'c' is 2, R1 is selected from the group consisting of C$_{1-16}$ alkanediyl, C$_{5-22}$ arylene, C$_{1-16}$ haloalkanediyl, C$_{3-12}$ cycloalkanediyl, C$_{1-20}$ heteroarenediyl, C$_{1-20}$ heterocyclicdiyl; when 'd' is 1, R2 is selected from the group consisting of C$_{1-16}$ alkyl, C$_{5-22}$ aryl, C$_{1-16}$ haloalkyl, C$_{3-12}$ cycloalkyl, C$_{1-20}$ heteroaryl, and C$_{1-20}$ heterocyclyl; when 'd' is 2, R2 is selected from the group consisting of C$_{1-16}$ alkanediyl, C$_{5-22}$ arylene, C$_{1-16}$ haloalkanediyl, C$_{3-12}$ cycloalkanediyl, C$_{1-20}$ heteroarenediyl, C$_{1-20}$ heterocyclicdiyl; 'a' and 'b' are in the range of 0-9, wherein 'a' and 'b' have values such that Xa-M$^{z+}$-Yb is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$, wherein the salts of R1(COOH)$_c$ and the salts of R2(COOH)$_d$ are independently selected from the group consisting of lithium salt, sodium salt, potassium salt, trialkylammonium salts, quaternary alkylammonium salts, and combinations thereof; (iii) water; and (iv) at least one organic solvent selected from the group consisting of hexane, toluene, xylenes, diesel, kerosene, naphtha, and combinations thereof at a temperature in the range of 30-80° C. to obtain a first mixture; and (b) stirring the first mixture at a temperature in the range of 30-80° C. for a period in the range of 1-10 hours to obtain the compound, wherein the: (a) transition metal salt to at least one carboxylate salt molar ratio in the first mixture is in the range of 1:2-1:6; (b) transition metal salt to water moles to volume ratio in the first mixture is in the range of 1:1.5-1:2; and (c) transition metal salt to at least one organic solvent moles to volume ratio in the first mixture is in the range of 1:2-1:4.

In an embodiment of present disclosure, there is provided a process for synthesis of compound of Formula:

$$X_a\text{-}M^{z+}\text{-}Y_b,$$

wherein $M^{z+}$ is a transition metal ion, wherein 'z' is in the range of 1-9; X and Y are anions of Formula R1(COO$^-$)$_c$ and R2(COO$^-$)$_d$ respectively, wherein 'c' and 'd' are independently in the range of 1-2; when 'c' is 1, R1 is selected from the group consisting of C$_{1-16}$ alkyl, C$_{5-22}$ aryl, C$_{1-16}$ haloalkyl, C$_{3-12}$ cycloalkyl, C$_{1-20}$ heteroaryl, and C$_{1-20}$ heterocyclyl; when 'c' is 2, R1 is selected from the group consisting of C$_{1-16}$ alkanediyl, C$_{5-22}$ arylene, C$_{1-16}$ haloalkanediyl, C$_{3-12}$ cycloalkanediyl, C$_{1-20}$ heteroarenediyl, C$_{1-20}$ heterocyclicdiyl; when 'd' is 1, R2 is selected from the group consisting of C$_{1-16}$ alkyl, C$_{5-22}$ aryl, C$_{1-16}$ haloalkyl, C$_{3-12}$ cycloalkyl, C$_{1-20}$ heteroaryl, and C$_{1-20}$ heterocyclyl; when 'd' is 2, R2 is selected from the group consisting of C$_{1-16}$ alkanediyl, C$_{5-22}$ arylene, C$_{1-16}$ haloalkanediyl, C$_{3-12}$ cycloalkanediyl, C$_{1-20}$ heteroarenediyl, C$_{1-20}$ heterocyclicdiyl; 'a' and 'b' are in the range of 0-9, wherein 'a' and 'b' have values such that Xa-M$^{z+}$-Yb is a neutral molecule; the process comprising the steps of: (a) contacting (i) a transition metal salt of Formula M-S, wherein M is a transition metal and S is a ligand selected from the group consisting of nitrate, sulfate, chloride, sulfite, and nitrite; (ii) at least one carboxylate salt selected from the group consisting of salts of R1(COOH)$_c$ and salts of R2(COOH)$_d$, wherein the salts of R1(COOH)$_c$ and the salts of R2(COOH)$_d$ are independently selected from the group consisting of lithium salt, sodium salt, potassium salt, trialkylammonium salts, quaternary alkylammonium salts, and combinations thereof; (iii) water; and (iv) at least one organic solvent selected from the group consisting of hexane, toluene, xylenes, diesel, kerosene, naphtha, and combinations thereof at a temperature of 40° C. to obtain a first mixture; and (b) stirring the first mixture at a temperature of 40° C. for a period of 3 hours to obtain the compound, wherein the: (a) transition metal salt to at least one carboxylate salt molar ratio in the first mixture is in the range of 1:2-1:6; (b) transition metal salt to water moles to volume ratio in the first mixture is in the range of 1:1.5-1:2; and (c) transition metal salt to at least one organic solvent moles to volume ratio in the first mixture is in the range of 1:2-1:4.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

Example 1: Preparation of Oil Soluble Co Based Catalyst SOSCAT-1

To a solution of cobalt (II) nitrate (1 eq.) in water and hexane (1:2 ratio; 5 ml per 1 mmol of Co salt), sodium 2-ethyl hexyl carboxylate (3 eq.) in water (solution of 1 mmol in 1 mL water) was added drop wise at 70° C. and the solution was refluxed for 3 h at 80° C. The resulting reaction mixture was cooled and fractionated between water/hexane layers. The organic layer was washed with the water. The organic phase was dried (Na$_2$SO$_4$), concentrated in vacuo to afford the cobalt carboxylate as a gummy solid. Yield: 94%; ICP-OES: 15.6% Co. IR, (neat, cm$^{-1}$): 1415; 1538; 1548; 2931; 2958.

Example 2: Preparation of Oil Soluble Fe Based Catalyst SOSCAT-2

To a solution of Iron (III) nitrate (1 eq.) in water and hexane (1:2 ratio; 5 ml per 1 mmol of Fe salt), sodium 2-ethyl hexyl carboxylate (4 eq.) in water (solution of 1 mmol in 1 mL water) was added drop wise at 40° C. and the solution was treated for 3 h at 40° C. The resulting reaction mixture was cooled and fractionated between water/hexane layers. The organic layer was washed with the water. The organic phase was dried ($Na_2SO_4$), concentrated in vacuo to afford the iron carboxylate as a gummy solid. Yield: 95%; ICP-OES: 7.02% Fe, IR, (neat, $cm^{-1}$): 1421; 1584; 1692; 2932; 2958; 2860.

Example 3: Preparation of Oil Soluble Ni based Catalyst SOSCAT-3

To a solution of Ni (II) nitrate (1 eq) in water and hexane (1:2 ratio; 5 ml per 1 mmol of Ni salt), sodium 2-ethyl hexyl carboxylate (3 eq.) in water (solution of 1 mmol in 1 mL water) was added drop wise at 70° C. and the solution was refluxed for 3 h at 80° C. The resulting reaction mixture was cooled and fractionated between water/hexane layers. The organic layer was washed with the water. The organic phase was dried ($Na_2SO_4$), concentrated in vacuo to afford the nickel carboxylate as a gummy solid.

Yield: 93%; ICP-OES: 8.5% Ni.

Example 4: Preparation of Oil Soluble Fe Based Catalyst SOSCAT-12

To a solution of iron (III) nitrate (1 eq.) in water and hexane (1:2 ratio; 5 ml per 1 mmol of Fe salt), sodium 2-ethyl hexyl carboxylate (4 eq.) in water (solution of 1 mmol in 1 mL water) was added drop wise at 40° C. and the solution was treated for 3 h at 40° C. The resulting reaction mixture was cooled and fractionated between water/hexane layers. The organic layer was washed with the water. The organic phase was dried ($Na_2SO_4$), concentrated in vacuo to afford the iron carboxylate as a gummy solid. Yield: 95%; ICP-OES: 7.02% Fe, IR, (neat, $cm^{-1}$): 1421; 1584; 1692; 2932; 2958; 2860. Subsequently with 0.5 wt % of benzoic acid is mixed with the above gummy solid in toluene and the solvent is removed to obtain the catalytic formulations.

Example 5: Preparation of Oil Soluble Fe Based Catalyst SOSCAT-13

To a solution of iron (III) nitrate (1 eq.) in water and hexane (1:2 ratio; 5 ml per 1 mmol of Fe salt), sodium 2-ethyl hexyl carboxylate (4 eq.) in water (solution of 1 mmol in 1 mL water) was added drop wise at 40° C. and the solution was treated for 3 h at 40° C. The resulting reaction mixture was cooled and fractionated between water/hexane layers. The organic layer was washed with the water. The organic phase was dried ($Na_2SO_4$), concentrated in vacuo to afford the Iron carboxylate as a gummy solid. Yield: 95%; ICP-OES: 7.02% Fe. IR (neat, $cm^{-1}$): 1421; 1584; 1692; 2932; 2958; 2860. Subsequently 4.9 wt % of benzoic acid is mixed with the above gummy solid in toluene and the solvent is removed to obtain the catalytic formulation.

Example 6: Preparation of Oil Soluble Fe Based Catalyst SOSCAT-16

To a solution of iron (II) sulphate (1 eq.) in water and hexane (1:2 ratio; 5 ml per 1 mmol of Fe salt), sodium 2-ethyl hexyl carboxylate (3 eq.) in water (solution of 1 mmol in 1 mL water) was added drop wise at 40° C. and the solution was treated for 3 h at 40° C. The resulting reaction mixture was cooled and fractionated between water/hexane layers. The organic layer was washed with the water. The organic phase was dried ($Na_2SO_4$), concentrated in vacuo to afford the iron carboxylate as a gummy solid. Yield: 90%; WD-XRF: 4.8% Fe.

Example 7: Preparation of Oil Soluble Fe Based Catalyst SOSCAT-17

To a solution of iron (III) nitrate (1 eq.) in water and hexane (1:2 ratio; 5 ml per 1mmol of Fe salt), sodium tridecanoate (4 eq.) in water (solution of 1 mmol in 1 mL water/THF (1:1)) was added drop wise at 40° C. and the solution was treated for 3 h at 40° C. The resulting reaction mixture was cooled and fractionated between water/hexane layers. The organic layer was washed with the water. The organic phase was dried ($Na_2SO_4$), concentrated in vacuo to afford the iron carboxylate as a gummy solid. Yield: 80%; WD-XRF: 4% Fe.

Example 8: Preparation of Oil Soluble Fe Catalyst SOSCAT-18

To a solution of iron (III) nitrate (1 eq.) in water and hexane (1:2 ratio; 5 ml per 1 mmol of Fe salt), potassium phthalate (2 eq.) in water (solution of 1 mmol in 1 mL water/THF (1:1)) was added drop wise at 40° C. and the solution was treated for 3 h at 40° C. The resulting reaction mixture was cooled and fractionated between water/hexane layers. The fractionation led to non-separated layers.

Example 9: Preparation of Oil Soluble Fe Based Catalyst SOSCAT-19

To a solution of iron (III) nitrate (1 eq.) in water and hexane (1:2 ratio; 5 ml per 1 mmol of Fe salt), sodium 2-ethyl hexyl carboxylate (2 eq.) and sodium tridecanoate (2 eq.) in water (solution of 1 mmol in 1 mL water) was added drop wise at 40° C. and the solution was treated for 3 h at 40° C. The resulting reaction mixture was cooled and fractionated between water/hexane layers. The organic layer was washed with the water. The organic phase was dried ($Na_2SO_4$), concentrated in vacuum to afford the iron carboxylate as a gummy solid. Yield: 92%; WD-XRF: 6.2% Fe.

As described above different catalysts were prepared/attempted using different metal salts and carboxylates. Characterization of the catalysts so obtained was carried out using wavelength dispersive X-ray fluorescence (WD-XRF) which indicated metal content in the catalyst. In some cases, metal content was determined using inductively coupled plasma optical emission spectrometry (ICP-OES). In case of SOSCAT-1 (Example 1) and SOSCAT-3 (Example 3), the reactions were carried out at 80 and 70° C. respectively. All other catalysts were prepared at 40° C. This is a significant leap from prior art methods, as almost all prior art methods synthesize these catalysts at or above 10° C. Some of the known methods employ temperatures as high as 150° C.

-200° C. The process for the synthesis of catalyst disclosed herein delightfully and surprisingly provided the required catalysts in excellent yields, at a modest temperature of 40° C. in most cases, and just a little over it (around 70° C.), in a couple of other cases.

Effect of Variation of Solvent

Experiments were also carried out, wherein reaction conditions were varied to see the effect of variation on reaction. Accordingly, catalyst synthesis was attempted using only water as a solvent.

Example 10: Preparation of Oil Soluble Fe Based Catalyst Using Water as a Solvent To a solution of iron (III) nitrate (1 eq.) in water (5 ml per 1 mmol of Fe salt), sodium 2-ethyl hexyl carboxylate (3 eq.) in water (solution of 1 mmol in 1 mL water) was added drop wise at 40° C. The resulting solution leads to gummy formation and clogging the stir bar. The reaction did not yield the desired product.

Thus, when catalyst synthesis was attempted using only water as a solvent, the catalyst could not be obtained.

Solubility of Catalysts in Various Solvents

As the main aim of the invention was to synthesize organometallic catalysts at lower temperatures, for use in hydrocracking process, a major requirement to achieve said end is solubility of the catalysts in the material to be hydrocracked. This material is a mostly a complex mixture of heavy oils, which by their very nature are carbon rich, lipophilic substances. Thus, good solubility of a certain catalyst in aliphatic, non-polar aromatic, and other non-polar lipophilic solvents can be safely taken as a pointer to good solubility of these catalysts in heavy oils to be hydrocracked. Accordingly, solubility studies were carried out on various catalysts of the instant disclosure. Results are summarized in Table 1 below.

TABLE 1

| Catalyst | Heptane | Toluene | Kero cut | Diesel | Water | Aq. NaOH solution | Aq. HCl solution |
|---|---|---|---|---|---|---|---|
| SOSCAT-1 | Yes | Yes | Yes | Yes | No | No | Slightly soluble |
| SOSCAT-2 | Yes | Yes | Yes | Yes | No | No | Slightly soluble |
| SOSCAT-3 | Yes | Yes | Yes | Yes | No | No | Slightly soluble |

As can be seen from the data in Table 1, all catalysts that were tested for solubility had excellent solubility in lipophilic solvents. This indicates their suitability for intended application, i.e., use in hydrocracking of heavy oils to transform them into lighter valuable products.

Example 11: Conversion of Heavy Oil Using Iron Based Oil Soluble Catalyst

In this example, the use of catalyst formulations thus produced in previous examples is explained. Initially, the reactor was fed with 50 g of hydrocarbon boiling above 350° C. along with oil soluble catalyst (SOSCAT-2) concentration of 2 wt % metal. The reactor was purged with nitrogen to remove any air trapped inside and later was pressurized to 12 MPa with hydrogen. The reaction mixture was heated to 420° C. under constant stirring at 1000 rpm to obtain a uniform slurry. The reaction was carried out for a period of 2 hour maintaining the reaction temperature at 420° C. After completing the reaction, the products were quenched by circulating chilled water to bring down the temperature below 300° C. rapidly.

The gaseous products were collected in a gas bomb and analyzed using gas chromatography for its composition. The liquid samples were collected and analyzed in GC-SIMDIST as per ASTM D-7169.

From the analyses of products, it was observed that the heavy hydrocarbon fraction in feed boiling above 350° C. converted into lighter hydrocarbons. The details are provided in Table 2.

Example 12: Conversion of Heavy Oil Using Iron Based Oil Soluble Catalyst Formulations In this example, the use of catalyst formulations thus produced in previous examples is explained. Initially, the reactor was fed with 50 g of hydrocarbon boiling above 350° C. along with oil soluble catalyst (SOSCAT-12) concentration of 1 wt % metal. The reactor was purged with nitrogen to remove any air trapped inside and later was pressurized to 12 MPa with Hydrogen. The reaction mixture was heated to 420° C. under constant stirring at 1000 rpm to obtain a uniform slurry. The reaction was carried out for a period of 2 hour maintaining the reaction temperature at 420° C. After completing the reaction, the products were quenched by circulating chilled water to bring down the temperature below 300° C. rapidly.

The gaseous products were collected in a gas bomb and analyzed using gas chromatography for its composition. The liquid samples were collected and analyzed in GC-SIMDIST as per ASTM D-7169.

From the analyses of products, it was observed that the heavy hydrocarbon fraction in feed boiling above 350° C. converted into lighter hydrocarbons. The details are provided in Table 2.

TABLE 2

| | | | | Product Yield | | |
|---|---|---|---|---|---|---|
| Experiment No | Catalyst Name | Concentration of Metal | Reaction Time | Gas | C5 to 350° C. cut | Above 350° C. cut |
| SHC-Run-124 | SOSCAT-2 | 2 wt % | 2 hours | 35% | 29% | 35% |
| SHC-Run-187 | SOSCAT-12 | 1 wt % | 2 hours | 16% | 34% | 50% |

It can be observed that the catalyst synthesized by the method as disclosed herein, effectively upgrades the heavy oil into lighter hydrocarbons. The examples provided here covers the range of formulations with and without aromatic acid. Depending upon the concentration of aromatic acid in the catalyst, the selectivity of the products can be obtained.

Although the subject matter has been described in considerable detail with reference to certain examples and implementations thereof, other implementations are possible.

Advantages gained in the Example Illustrative Process in this Subject Matter The present disclosure thus provides a superior process for the preparation of hydrocarbon soluble transition metal catalysts with potential applications in hydrocracking of heavy oils. The preparation process of the instant disclosure is a low-temperature process, wherein in most cases synthesis of the catalyst can be achieved at temperatures as low as 40° C., which is hitherto unknown.

We claim:

1. A process for synthesis of a compound, the process comprising:
   (a) contacting (i) a transition metal salt of Formula M-S, wherein M is Fe3+ and S is a ligand selected from the group consisting of nitrate, sulfate, chloride, sulfite, and nitrite; (ii) at least one carboxylate salt selected from the group consisting of salts of $R1(COOH)_c$ and salts of $R2(COOH)_d$, wherein $R1(COOH)_c$ and $R2(COOH)d$ are respectively 2-ethylhexanoic acid and tridecanoic acid; (iii) water; and (iv) at least one organic solvent to obtain a first mixture, wherein contacting is carried out at a temperature of 40° C.; and
   (b) stirring the first mixture to obtain the compound, wherein the compound has a formula $X_a\text{-}M^{z+}\text{-}Y_b$, wherein, $M^{z+}$ is $Fe^{3+}$; X and Y are independently selected from the group consisting of 2-ethyl hexyl carboxylate and tridecanoate; and 'a' and 'b' are in the range of 0-3, wherein 'a' and 'b' have values such that $X_a\text{-}M^{z+}\text{-}Y_b$ is a neutral molecule.

2. The process as claimed in claim 1, wherein (a) the transition metal salt to the at least one carboxylate salt molar ratio in the first mixture is in the range of 1:2-1:6; (b) the transition metal salt to water moles to volume ratio in the first mixture is in the range of 1:1.5-1:2; and (c) the transition metal salt to the at least one organic solvent moles to volume ratio in the first mixture is in the range of 1:2-1:4.

3. The process as claimed in claim 1, wherein the salts of $R1(COOH)_c$ and the salts of $R2(COOH)_d$ are independently selected from the group consisting of lithium salt, sodium salt, potassium salt, trialkylammonium salts, quaternary alkylammonium salts, and combinations thereof.

4. The process as claimed in claim 1, wherein the at least one organic solvent is selected from the group consisting of hexane, toluene, xylenes, diesel, kerosene, naphtha, and combinations thereof.

5. The process as claimed in claim 1, wherein stirring the first mixture to obtain the compound is carried out at a temperature in the range of 30-80° C. for a period in the range of 1-10 hours.

6. The process as claimed in claim 1, wherein stirring the first mixture to obtain the compound is carried out at a temperature of 40° C. for a period of 3 hours.

\* \* \* \* \*